US012752042B2

(12) United States Patent
Bourquin et al.

(10) Patent No.: US 12,752,042 B2
(45) Date of Patent: Oct. 6, 2026

(54) BREAST PUMP DEVICE AND CONTROLLER FOR THE DEVICE, AND A CONTROL METHOD

(71) Applicant: KONINKLIJKE PHILIPS N.V., Eindhoven (NL)

(72) Inventors: Yannyk Parulian Julian Bourquin, Eindhoven (NL); Lili-Marjan Brockhuis, Geldrop (NL); Lucja Elzbieta Segaar, Oirschot (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 790 days.

(21) Appl. No.: 18/026,357

(22) PCT Filed: Sep. 10, 2021

(86) PCT No.: PCT/EP2021/074966
§ 371 (c)(1),
(2) Date: Mar. 15, 2023

(87) PCT Pub. No.: WO2022/058248
PCT Pub. Date: Mar. 24, 2022

(65) Prior Publication Data

US 2023/0355850 A1 Nov. 9, 2023

(30) Foreign Application Priority Data

Sep. 21, 2020 (EP) .................................... 20197128

(51) Int. Cl.
*A61M 1/06* (2006.01)

(52) U.S. Cl.
CPC ... *A61M 1/0693* (2021.05); *A61M 2205/3306* (2013.01); *A61M 2205/3331* (2013.01); *A61M 2205/50* (2013.01)

(58) Field of Classification Search
CPC .... A61M 1/06; A61M 1/0697; A61M 1/0693; A61M 1/069; A61M 1/068; A61M 2205/8212
See application file for complete search history.

(56) References Cited

U.S. PATENT DOCUMENTS

2012/0116298 A1 * 5/2012 Van Schijndel ........ A61M 1/06
604/74
2016/0206794 A1 7/2016 Makower
(Continued)

FOREIGN PATENT DOCUMENTS

CN 103028156 A 4/2013
WO 0057934 A1 10/2000
(Continued)

OTHER PUBLICATIONS

International Search report and Written Opinion of PCT/EP2021/074966, dated Dec. 9, 2021.

*Primary Examiner* — Deanna K Hall

(57) ABSTRACT

A breast pump device is provided and a controller for operating a pressure source of the breast pump device. A milk flow is monitored during a breast pumping session. The pressure source is controlled in dependence on the flow, thereby to switch, during the breast pumping, between a first pressure profile of the pressure source for a low energy mode and a second pressure profile of the pressure source for an expression mode. The breast pumping session comprises a plurality of time periods with the low energy mode and a plurality of time periods with the expression mode, in order to reduce electrical power consumption.

19 Claims, 5 Drawing Sheets

(56) References Cited

U.S. PATENT DOCUMENTS

| | | | | |
|---|---|---|---|---|
| 2017/0021068 | A1* | 1/2017 | Gaskin | A61M 1/06 |
| 2018/0110906 | A1* | 4/2018 | Barack | A61M 1/06935 |
| 2018/0361040 | A1 | 12/2018 | O'Toole et al. | |
| 2020/0078503 | A1 | 3/2020 | Bartlett et al. | |

FOREIGN PATENT DOCUMENTS

| | | | |
|---|---|---|---|
| WO | 2011010255 | A1 | 1/2011 |
| WO | 2016014469 | A1 | 1/2016 |

* cited by examiner

BREAST PUMP DEVICE AND CONTROLLER FOR THE DEVICE, AND A CONTROL METHOD

CROSS-REFERENCE TO PRIOR APPLICATIONS

This application is the U.S. National Phase application under 35 U.S.C. § 371 of International Application No. PCT/EP2021/074966, filed on Sep. 10, 2021, which claims the benefit of European Patent Application No. 20197128.0, filed on Sep. 21, 2020. These applications are hereby incorporated by reference herein.

FIELD OF THE INVENTION

The invention relates to a breast pump device and a method of operating a breast pump device.

BACKGROUND OF THE INVENTION

Breast pumps are used by breast feeding women to extract milk from their breast such that the extracted milk can be fed to their babies at a later time.

It is well known that the best nutrition for babies is breast milk. The world health organization (WHO) recommends to breast feed babies for at least one year, preferably longer. However, mothers often go back to work after only several weeks or months. To provide the best nutrition to their babies, mothers may then express milk using a breast pump. The expressed milk can be stored and given to the baby at a later stage and/or by somebody else.

Typically, the breast is placed into a funnel shaped cup and a vacuum is applied such that milk is extracted. Breast pumps typically have a stimulation mode to activate the milk ejection reflex (MER), and an expression mode.

Typically, the transition from the stimulation mode to the expression mode is not based on detection of MER. It is either time-based, i.e. a fixed time after switching on, or manually controlled by pushing a button.

It has been recognized that automatic detection of the MER may be used to switch automatically between different modes.

WO 2011/010255 discloses a breast pump with many modes, including a stimulation mode (called a let-down mode) and an expression mode. It can switch from the stimulation mode to the expression mode automatically, based on various sensed values.

Once in the expression mode, the breast feeding session continues until a defined quantity of milk has been collected, or a defined time has elapsed, or the mother chooses to stop.

US 2020/0078503 discloses a breast pump in which the sensing of milk flow parameters is used to control automatically the breast pumping process. One proposed mode of operation alternates between a stimulation mode and an expression mode.

WO 2016/014469 discloses a breast pump having a sensor e.g. for measuring pressure, so that pressure waveforms may be plotted during operation of the breast pump. The waveforms can be used to determine when milk flow initiates. Cycle frequencies or pressure amplitudes can be controlled based on feedback to optimize milk extraction.

WO 00/57934 discloses a breast pump which implements a non-nutritive sucking cycle (i.e. a stimulation cycle with rapidly repeating low vacuum pulses) and a nutritive sucking cycle (i.e. an expression cycle with slowly repeating stronger vacuum pulses).

Many breast pumps are battery operated, in order to make them portable. Electrical power consumption is then an issue, and it would be desirable to operate the breast pump as electrically efficiently as possible. The expression mode however consumes a large amount of power, due to the high vacuum level (high under-pressure) that is applied.

SUMMARY OF THE INVENTION

The invention is defined by the claims.

According to examples in accordance with an aspect of the invention, there is provided a controller for a breast pump device, wherein the controller is for controlling operation of a pressure source of the breast pump device to apply an under-pressure, the controller comprising:

- an input for receiving an input signal relating to a milk flow during a breast pumping session using the breast pump device; and
- an output for controlling operation of the pressure source in dependence on the input signal, thereby to switch, during the breast pumping, from a low energy mode with a first pressure profile of the pressure source to an expression mode with a different second pressure profile of the pressure source, and to switch from the expression mode to the low energy mode.

There is also a stimulation mode with a third pressure profile of the pressure source, wherein the first to third pressure profiles are all different. The output is then for controlling operation of the pressure source to follow a sequence comprising the stimulation mode followed by alternating expression modes and low energy modes. The low energy mode uses less power than either the stimulation mode or the expression mode.

The breast pumping session thus comprises a plurality of time periods with the low energy mode and a plurality of time periods with the expression mode.

This controller monitors the milk flow during (rather than only at the start) of a breast pumping session, so that throughout the breast pumping session the breast pump may be switched between a low energy mode and an expression mode. The expression mode is used at times when milk is flowing, and the low energy mode is used at times when the milk flow has stopped, or is declining (so indicating an end of a period of expression), or has dropped below a threshold level. In this way, the time duration of the most electrically power demanding mode i.e. the expression mode, can be kept to a minimum. There may be multiple low energy mode times and multiple expression mode times (depending on the profile of the milk flow of the mother).

A breast pumping session starts with a stimulation mode, followed by an expression mode. However, the expression mode is interrupted with the low energy modes.

Thus, stimulation is at the beginning of breast pumping, and there are then low energy modes distributed with the expression modes throughout the breast pumping session.

The low energy mode has a different pressure profile to both the initial stimulation mode and the expression mode. It may for example have a frequency corresponding to the expression mode but a lower under pressure level. It may have different dwell in time or dwell out time compared to the expression mode.

The low energy mode is "low energy" in that it has lower electrical power consumption (i.e. energy usage per unit time) than the expression mode or the stimulation mode.

The invention is in part based on the recognition that within the time generally considered to be the milk expression time, there are time periods of high milk flow and time periods of low or no milk flow, creating a locally varying milk flow pattern. The low energy mode is used during the periods of low or no milk flow. The low energy mode may be considered to be any mode which maintains a cyclic pressure waveform, suitable while waiting for milk expression. It has a different pressure profile to the expression mode, in particular a reduced maximum under-pressure level as it is intended to save power rather than achieve the greatest milk flow. It also has a different pressure profile to the initial stimulation mode.

The breast pumping session preferably comprises a continuous sequence of the time periods of the low energy mode and the expression mode.

There may be different types of pressure profile for the low energy mode and different types of pressure profile for the expression mode. The continuous sequence means that these different modes (with the same pressure profile each time or with different pressure profiles) are used multiple times in the same session (rather than once each is separate sessions).

As mentioned above, the low energy mode has a lower electrical power consumption than the expression mode and a lower electrical power consumption than the stimulation mode. Thus, by switching from the expression mode to the low energy mode whenever the sensed milk flow makes it appropriate, power savings are obtained.

The low energy mode for example has a lower maximum under-pressure level than the expression mode. This enables the reduced power consumption. The expression mode for example has a maximum under-pressure above 200 mbar (20 kPa) and the low energy mode has a maximum under-pressure below 200 mbar (20 kPa). The under-pressure level is the pressure level relative to (and below) the ambient pressure level.

The input signal may indicate the detection of (one or more of) milk drops or a cumulative milk flow or a milk flow gradient or a trend in the milk flow gradient. In each case, the input signal can be used to indicate that a local period of milk expression is coming to an end or has ended.

The controller may be adapted to derive a relationship between the cumulative milk flow and time for a particular user, and to derive a program of operation of the pressure source for the particular user from the relationship. Thus, the controller can learn from the sensing to derive a customized pressure sequence for a particular user. This customized pressure sequence may then have lower power consumption than when sensing feedback is used, because the sensor may then be deactivated.

The invention also provides breast pump device, comprising

- at least one breast receiving portion configured to receive a breast of a user;
- a pressure source coupled to the at least one breast receiving portion and being configured to generate at least an under-pressure;
- a sensor for generating said input signal relating to the milk flow during a breast pumping session; and
- the controller defined above.

The sensor for example comprises an optical sensor. This may be used to detect the passage of milk droplets during breast pumping, for example between the breast receiving portion and a collection vessel.

The sensor for example comprises an optical emitter arrangement, an optical detector arrangement and an output for providing a signal indicating the presence milk expressed.

The device preferably comprises a battery-operated device. Thus, the electrical efficiency gains enable a prolonged battery life.

The invention also provides a computer-implemented non-therapeutic method of controlling a breast pump device, the breast pump device comprising at least one breast receiving portion configured to receive a breast of a user and a pressure source coupled to the at least one breast receiving portion and being configured to generate at least an under-pressure, the method comprising:

- receiving an input signal relating to a milk flow during a breast pumping session using the breast pump device; and
- controlling operation of the pressure source in dependence on the input signal, thereby to switch, during the breast pumping, from a low energy mode with a first pressure profile of the pressure source to an expression mode with a different second pressure profile of the pressure source, and to switch from the expression mode to the low energy mode.

There is also a stimulation mode with a third, pressure profile of the pressure source, wherein the first to third pressure profiles are all different. The method comprises controlling operation of the pressure source to follow a sequence comprising the stimulation mode followed by alternating expression modes and low energy modes.

The breast pumping session thus may comprise a plurality of time periods with the low energy mode and a plurality of time periods with the expression mode.

The low energy mode preferably has a lower electrical power consumption and a lower maximum under-pressure level than the expression mode. The input signal indicates the detection of milk drops or a milk flow level or a milk flow gradient.

Compared to the expression mode, the low energy mode for example has:

- a lower electrical power consumption; and
- a lower maximum under-pressure level and/or a longer dwell in time and/or a longer dwell out time and/or a longer rising time.

The method may be implemented in software.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
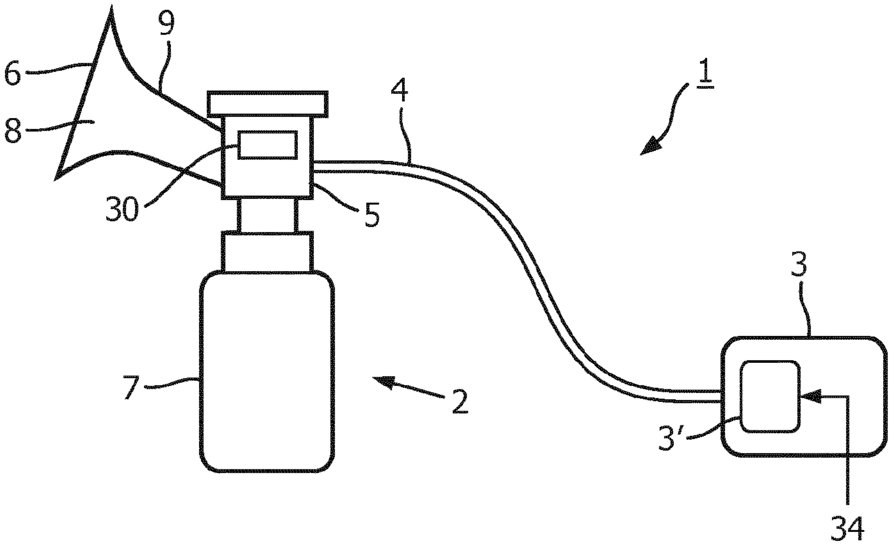
FIG. 1 shows a breast pump system in accordance with the invention.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a breast pump device and a controller for operating a pressure source of the breast pump device. A milk flow is monitored during a breast pumping session. The pressure source is controlled in dependence on the flow, thereby to switch, during the breast pumping, between a first pressure profile of the pressure source for a low energy mode and a second pressure profile of the pressure source for an expression mode. The breast pumping session may then for example comprise a plurality of time periods with the low energy mode and a plurality of time periods with the expression mode, in order to reduce electrical power consumption.

FIG. 1 shows a breast pump system in accordance with the invention.

The basic known parts will first be described. The breast pump system 1 comprises a breast pump 2, also known as an expression unit, and an operating unit 3. The operating unit is basically a pump unit (vacuum pump), associated hardware, and a pump controller 3'.

The breast pump 2 and the operating unit 3 are connected by a hose 4. The hose 4 provides a fluid communication between the breast pump 2 and the operating unit 3. The hose 4 may also be used to provide an electrical connection between the breast pump 2 and the operating unit 3. For example, the hose 4 may supply an operating signal or electrical power between the breast pump and the operating unit. In an alternative embodiment, the operating unit 3 is directly mounted and connected to the breast pump 2.

The breast pump 2 has a main body 5, a funnel 6 and a collection vessel 7. The collection vessel 7 collects milk expressed from a user's breast and may take the form of a feeding bottle or bag or any suitable container. The collection vessel 7 is attached to the main body 5 by a screw fitting, although it will be understood that alternative releasable attachment means may be used, such as clips (not shown).

The breast-receiving funnel 6 extends from the main body 5. The funnel 6 is configured to receive the breast of a user. The funnel 6 has a mouth 8 and a throat 9. The mouth 8 is open at an outer end of the funnel 6 to receive a user's breast, and the funnel 6 converges from the outer end towards the throat 9 to form a hollow recess in which a breast is received.

The main body 5 fluidly connects the funnel 6 to the collection vessel 7. A fluid passageway 10 (shown in FIG. 2) is formed through the main body 5 from the breast receiving space of the funnel 6 to the collection vessel 7. The main body 5 is formed from an outer shell. The main body 5 is integrally formed with the funnel 6, however it will be understood that the funnel 6 may be detachable. In the present arrangement, the main body 5 is formed from polypropylene, although it will be understood that alternative suitable materials may be used.

In addition to the standard parts as described above, FIG. 1 shows a sensor 30 for sensing milk flow information. The controller 3' uses this information to adapt the pressure profile applied, as explained below.

Figure 2:
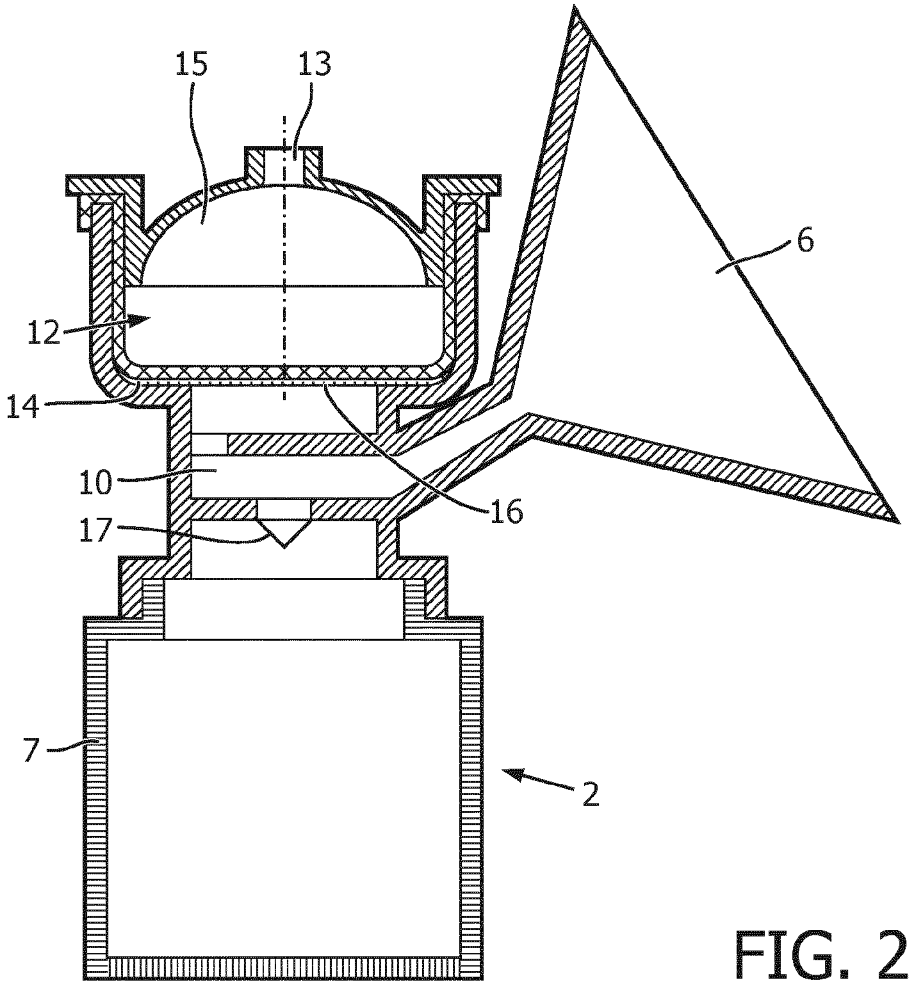
FIG. 2 shows one example of breast pump design in more detail.

Referring now to FIG. 2, a chamber 12 is formed in the main body 5. The chamber forms part of a vacuum path. The chamber 12 is in fluid communication with the fluid passageway 10 between the funnel 6 and the collection vessel 7. The chamber 12 has a vacuum port 13. The vacuum port 13 provides a port to communicate with the operating unit 3. The hose 4 is mountable to the vacuum port 13 to fluidly connect the chamber 12 with the operating unit 3.

A membrane 14 is received in the chamber 12. The membrane 14, also known as a diaphragm, is flexible. An outer rim of the membrane 14 is mounted to the chamber 12. The membrane 14 separates the chamber 12 into a first space 15 and a second space 16. The first space 15 communicates with the vacuum port 13. The first space 15 forms part of a first section of the vacuum path. The second space 16 communicates with the fluid passageway 10 between the breast receiving space of the funnel 6 and the collection vessel 7. The second space 16 forms part of a first section of the vacuum path.

A one-way valve 17 is disposed in the fluid passageway 10. The one-way valve 17 prevents a pressure reduction being formed in the collection vessel 7. The one-way valve is for example a duckbill valve.

The membrane 14 is for example formed from silicone. However, it will be understood that the membrane 14 may be formed from another suitable material.

The flexible membrane 14 has a predefined shape. In the present arrangement, the membrane 14 has a substantially cup-shaped arrangement in a neutral condition. That is, when the membrane 14 is received in the chamber 12, but has not been deformed. However, it will be understood that the membrane 14 may have an alternative shape.

The operating unit 3 comprises a pump controller 3', a power source, a motor and a pump unit actuated by the motor. The pump unit is configured to generate and release a pressure reduction (i.e. vacuum) in the vacuum path, for example using a pressure relief valve separate to the pump unit, although these may be combined into a single unit. The controller 3' controls operation of these components of the operating unit 3.

The controller 3' operates the pump unit with sequence of strokes, each stroke comprising the vacuum generation phase and the vacuum release phase. During vacuum generation, the breast is stimulated to express milk. This milk flows to the fluid passageway 10. During the vacuum release phase, the milk passes through the one-way valve 17 into the collection vessel. A small opening is for example provided to allow air to escape from the bottle. This may be located at the screw connection.

This is only one example of breast pump design. The invention relates to the pressure profile applied during a breast pump session, and may be applied to any known breast pump design.

Figure 3:
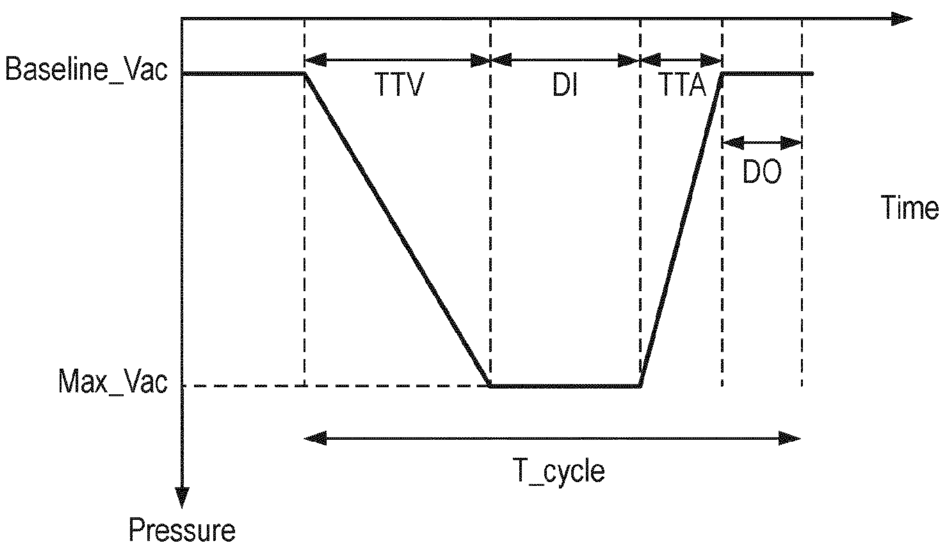
FIG. 3 shows in schematic form an example of a typical pressure cycle during expression.

FIG. 3 shows in schematic form an example of a typical pressure cycle during expression, applied by the pump unit of the operating unit 3.

The control signal to the pump unit, and hence the pressure, cycles between a baseline vacuum "Baseline_Vac" and a maximum vacuum (i.e. a maximum under-pressure) "Max_Vac".

There is first a time to (maximum) vacuum, TTV, then a dwell-in time DI, then a time to atmosphere (or to the baseline vacuum), TTA, and finally a dwell-out time, DO. The vacuum rate is defined as Max_Vac/TTV and the atmospheric rate is defined as Max_Vac/TTA.

By way of example:

Baseline_Vac=atmospheric pressure

Max_Vac=300 mbar (30 kPa) below atmospheric pressure

TTV=0.85 s

DI 32 0.3 s

TTA=0.05 s

DO=0.35 s

This gives a total cycle time T cycle of 1.55 s.

These values are simply by way of example. The maximum under-pressure may be higher, for example 350 mbar (35 kPa) and the the durations may differ. The cycle time is generally of the order of 1 to 2 seconds.

Figure 4:
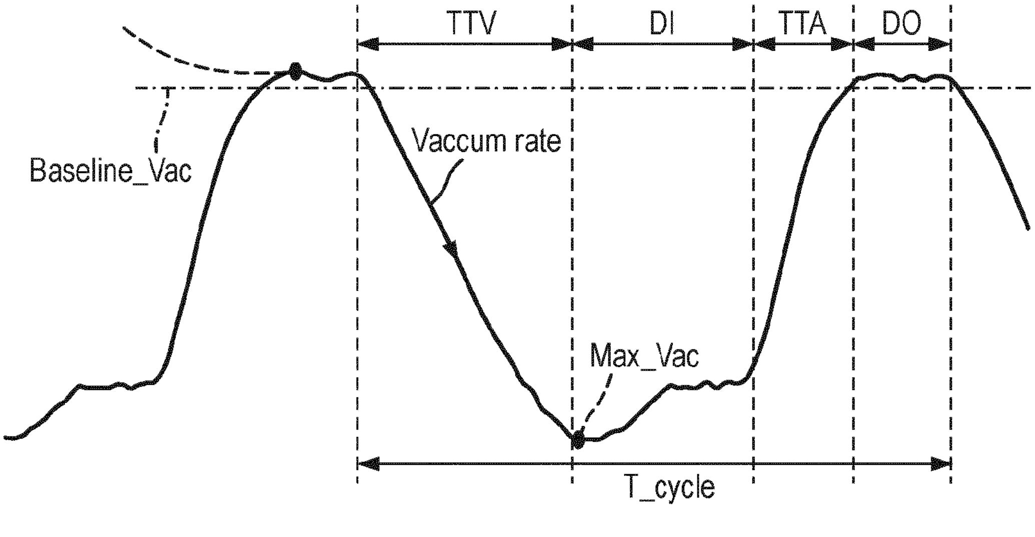
FIG. 4 shows a more realistic pressure waveform.

FIG. 4 shows a more realistic pressure waveform. It also shows an arrow representing the vacuum rate.

During a breast pumping session, the milk flow pattern evolves mainly due to the occurrence of milk ejection reflex (MER). Thus, within one session, several MERs can occur.

Figure 5:
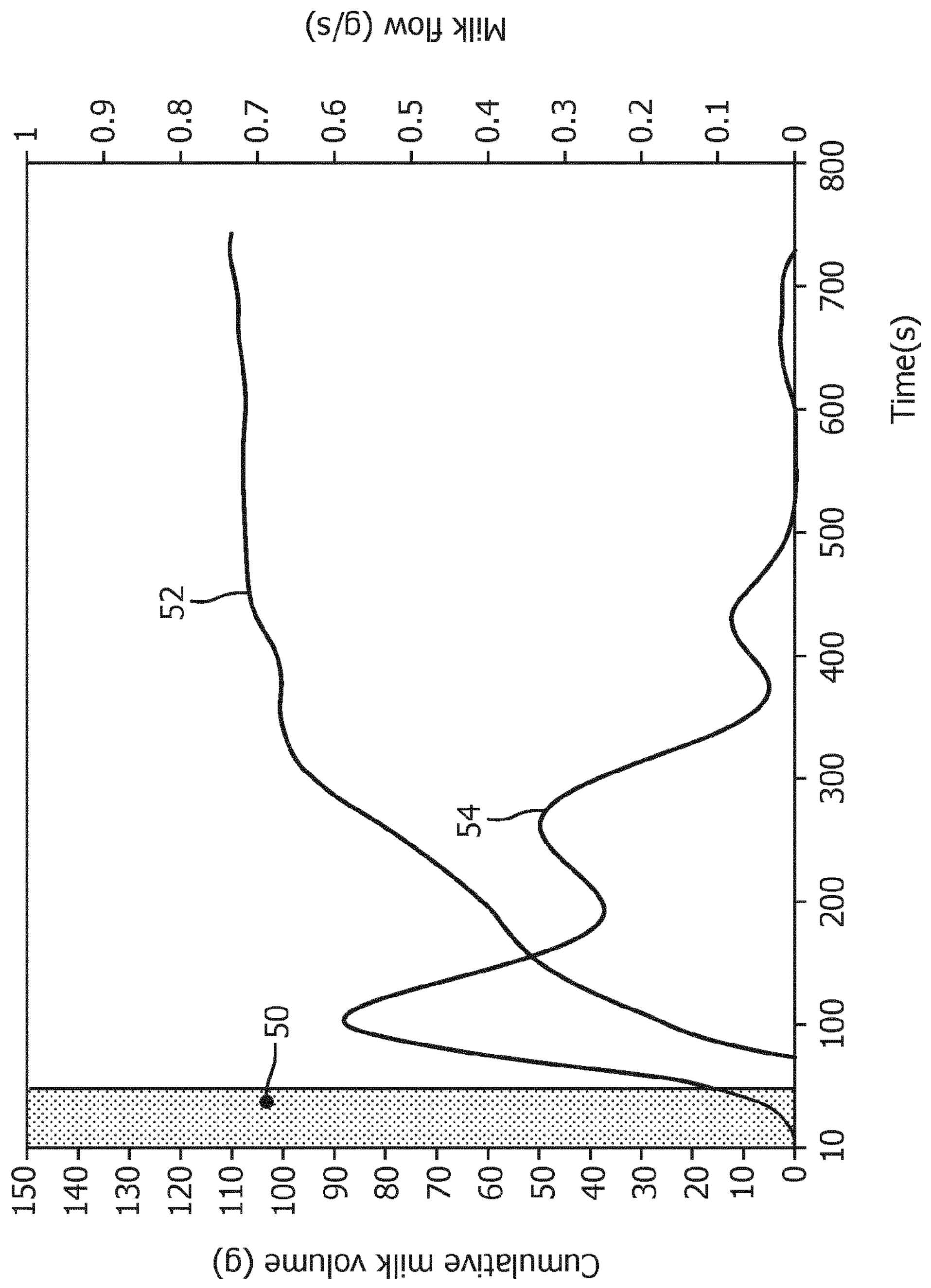
FIG. 5 shows a typical milk expression pattern during a breast pumping session.

A typical pattern is shown in FIG. 5 for a full breast pumping session of 800 seconds. A stimulation mode takes place during time period 50, for example with duration 50 seconds. The stimulation mode has a faster frequency hence with a shorter cycle time of around 0.5 seconds, and a lower vacuum, for example a maximum under-pressure level of 150 mbar (15 kPa). The expression mode conventionally takes place during the remainder of the breast feeding session.

Plot 52 shows the cumulative mass of milk collected over time (using the left y-axis scale, grams). Plot 54 shows the milk flow rate (using the right y-axis scale, g/s) hence the first derivative of plot 52. The derivative of the flow rate signal 52 (not shown) has positive periods when the flow rate is increasing and negative periods when the flow rate is decreasing.

The invention provides a system for controlling the pressure source to switch between the expression pressure profile and and a low energy pressure profile (in both directions) and typically multiple times during a breast pumping session. The different pressure profiles are chosen in dependence on the milk flow, captured by means of the sensor 30.

Figure 6:
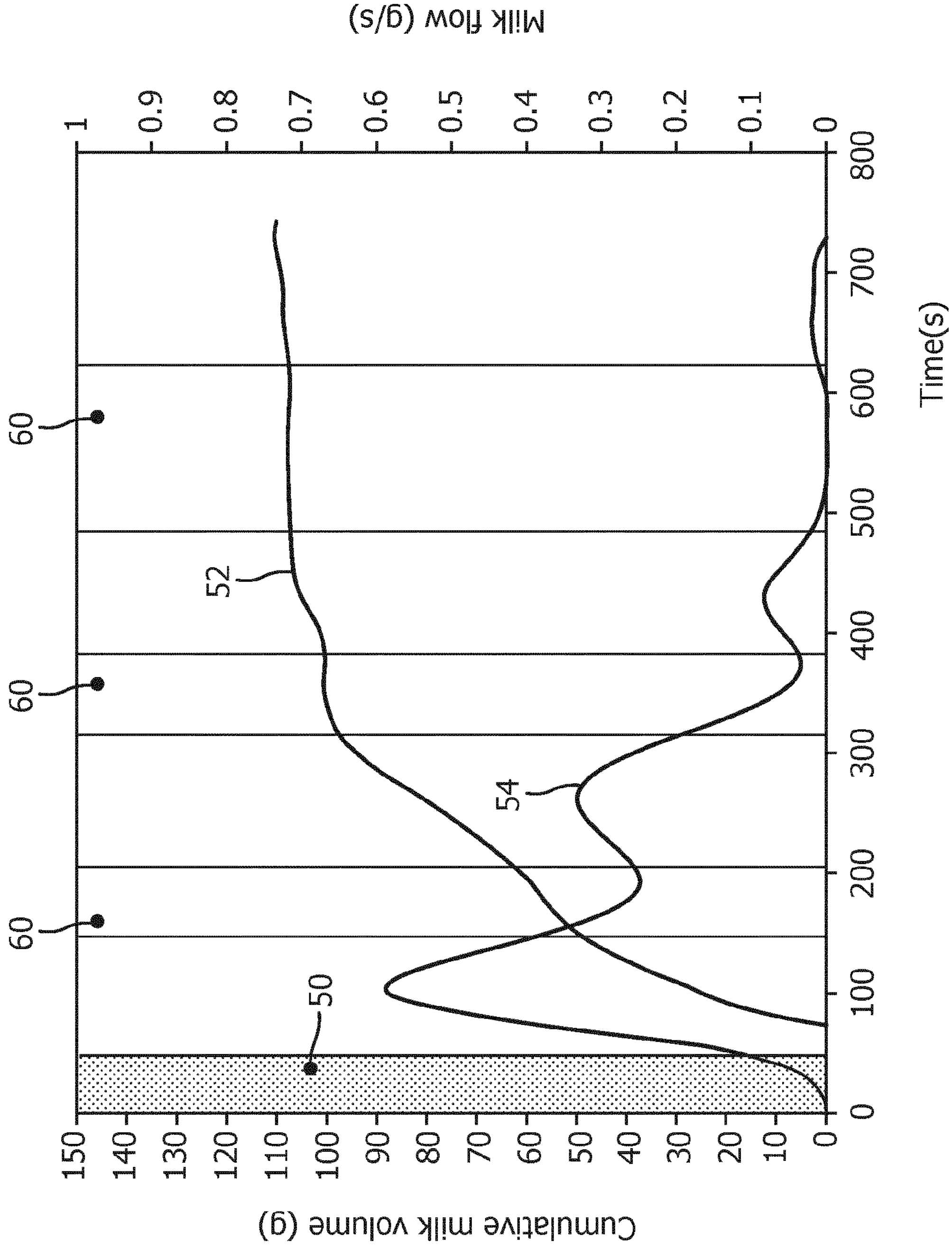
FIG. 6 shows the same plots as FIG. 5, but shows that a low energy mode (such as a stimulation mode) may be used multiple times within the breast feeding session.

FIG. 6 shows the same plots as FIG. 5, but shows that the low energy mode may be used multiple times within the breast feeding session. Three additional periods 80 of a low energy mode have been added.

The switching to the low energy mode may be based on analysis of the cumulative milk volume (curve 52) or milk flow rate (curve 54) or trends in the milk flow rate (derivative of curve 54). FIG. 6 shows that a drop in the milk flow rate from a local peak, by a given amount, indicates that an expression period is coming to an end. A particular gradient threshold of the milk flow rate (i.e. when curve 54 is increasing at a certain rate) may for example be used to trigger the expression mode.

One example involves switching to the low energy mode when a drop in milk flow rate (plot 54) from a local peak has been detected, e.g. a 30% drop. This triggers a switch in the vacuum profile setting. Similarly, an increase of milk flow rate by a certain amount from a local minimum may be used to switch back to the expression mode.

Another example is to detect the slope of the milk flow rate profile 54, and switch to the low energy mode when the slope has a transition from positive to negative. The system can switch to the expression mode when the slope has a transition from negative to positive. A waiting time may be implemented before the switch, e.g. 10 seconds, after the transition to a negative slope to allow completion of that local period of milk expression.

It can be seen that various measures may be used to detect when to implement the mode transitions.

Thus, there is a plurality of time periods with the low energy mode (3 in this example plus the initial stimulation mode) and a plurality of time periods (4 in this example) with the expression mode. They alternate as shown and define overall a continuous time sequence (i.e. they are part of the same breast pumping session).

There may for example be 1 to 10 low energy mode periods (in addition to the initial stimulation mode) and 2 to 10 expression mode periods, depending on the feeding characteristics of the mother. The number will depend on the number of MERs, which is typically from 1 to about 10.

The time periods of the low energy mode for example have a lower under-pressure than the expression mode, for example with the 15 kPa under-pressure of the stimulation mode instead of the 30 kPa under-pressure of the expression mode. They may instead have an even lower under-pressure than the stimulation mode.

The low energy mode may comprise a long duration cycle, thereby reducing the switching energy. The low energy mode cycles may for example have the same period as time periods of the expression mode, i.e. the longer duration (e.g. 1.5 s) cycles explained above.

The low energy mode may have different time profile and pressure levels to both the stimulation mode and the expression mode.

The low energy mode may for example have the same rise and fall times (TTV, TTA) of the expression mode, but with increased dwell in time DI and/or and dwell out time DO thereby extending the cycle to be longer than the cycle time of the expression mode.

The low energy mode may for example have a longer (i.e. lower gradient i.e. slower) rising time (TTV). Again, this will extend the cycle period.

In all cases, the low energy mode is designed to reduce power consumption while still enabling expression to be restarted.

The breast pump thus switches both from the stimulation mode to the expression mode (as is known) and also switches from the expression mode to the low energy mode when it is detected that a short term localized (in time) period of expression is coming to an end or has come to an end. The breast pump then toggles between the low energy mode and the expression mode.

The sensing to determine when to switch between modes may be performed in various ways.

Figure 7:
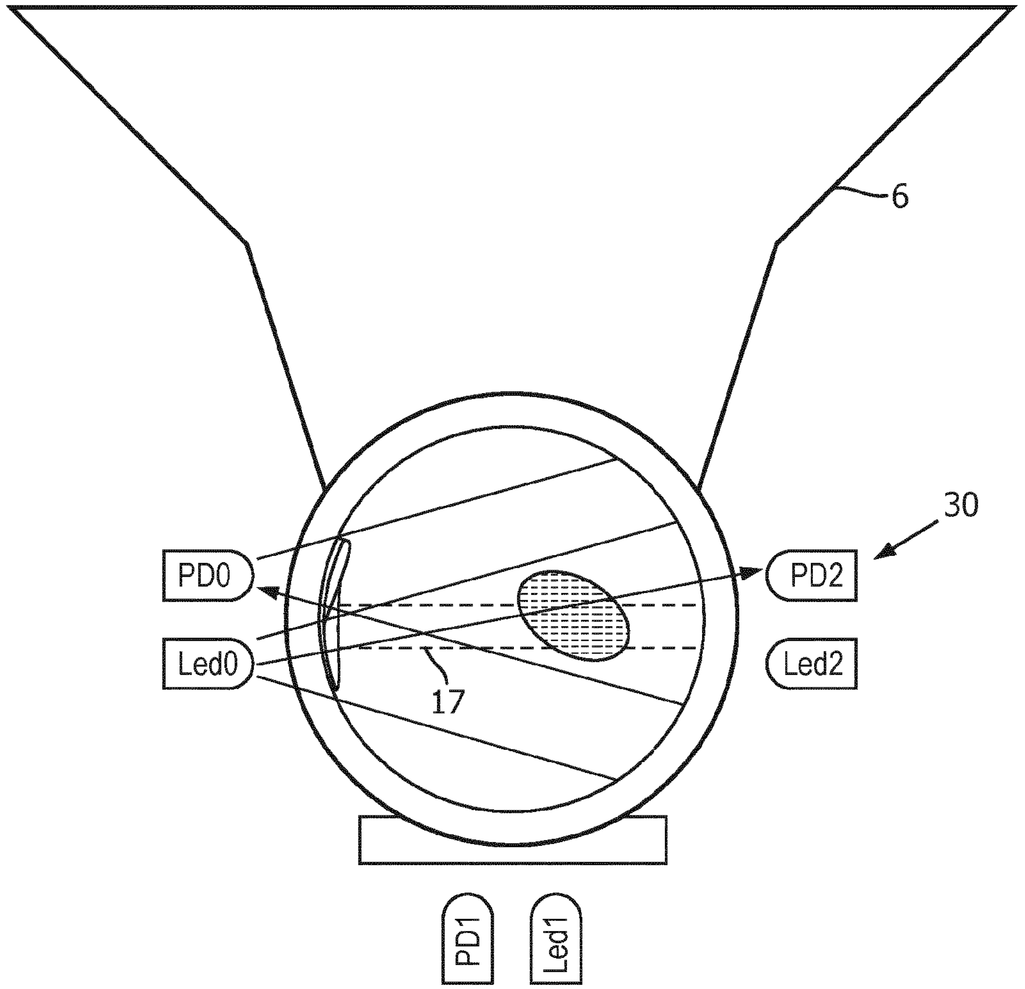
FIG. 7 shows an example of the sensor implemented as an optical sensor.

FIG. 7 shows an example of the sensor 30 implemented as an optical sensor located at the neck portion of the expression kit. It shows a cross section through the fluid passageway 10 looking from above. It shows the valve 17 and a milk droplet 60 at the valve. Expressed milk passes this neck portion before it reaches the bottom of the collection vessel. Droplets can thereby be sensed as they pass the neck portion.

The detection may be based on detecting the interruption of a light beam, or it may be based on measurement of a change in reflection or scattering of light back from a layer of milk on the inner wall of the expression kit.

In this example, the optical sensor may comprise a snap-on holder, which can snap onto the neck portion of the expression kit.

The emitter or emitters and detector or detectors may be mounted externally of the expression kit. The design may make use of the diffuse properties of the material used for making the expression kit, such as silicone. As emitter, a LED having a large divergence angle (approximately 120 degrees) may be used as the illumination source and the light that exits internally after passage through the material exhibits a near diffuse illumination pattern illuminating the whole head of the bottle. This enables to detect any small changes in the intensity on a detector due to the changes in the absorption and scattering induced by the flowing milk. Thus, it may suffice to have a single emitter and a single detector.

The example of FIG. 9 instead comprises three emitters (LEDs) Led0, Led1, Led2 and three detectors (photodiodes) PD0, PD1, PD2. The signals obtained from the detectors are processed to determine the presence of a milk drop based on changes in the intensity of light detected in all detectors.

Other sensor designs are possible, for example based on acoustic sensing (sensing the sound of a falling droplet). Indeed, any known sensor design may be used for detecting or measuring a flow of liquid.

In the example above, the presence of milk drops is sensed and used to switch between settings. For example, the low energy mode is switched on when no milk is detected and the expression mode is switched on when a drop is detected. Alternatively, the switching may be based on a threshold level of the milk flow volume, i.e. when a certain additional amount of flow has taken place (rather than just droplet). Alternatively, the switching may be based on the slope of the milk flow volume, i.e. the gradient of the milk flow volume curve and hence the flow rate.

The switching may be based on the trend of the milk flow rate i.e. the second derivative of the milk flow volume curve. Typically, when the flow rate is reducing (negative second derivative), the pump can be switched to the low energy mode, and when the milk flow rate is increasing (positive second derivative), the pump can be switched to the expression setting.

Thus, the sensing may be for droplet detection, for detection of a flow amount, for detection of a flow rate, or for detection of a trend in the flow rate. Any or all of these measures may be used to determine times when expression is taking place and times when it is ending or has ended.

In a simplest implementation, the breast pump has only the stimulation mode, which functions as the low energy mode, and the expression mode. However, there may be other modes, such as a massage mode and the low energy mode may be different to the initial stimulation mode.

When the user switches on the pump, an initial stimulation mode is active. When milk starts flowing, the sensor detects the milk and switches the pump setting to the expression mode. When the milk flow rate is reduced to a certain level, the pump is then switched back to the low energy mode (e.g. the stimulation mode) to save energy.

When the milk flow increases again, the pump is again switched to the expression mode.

The effect of the power saving approach of the invention on the collection of milk has been assessed based on a volunteer study with two types of vacuum profile settings applied to multiple volunteers.

The first type was the standard expression setting with a maximum under pressure of 350 mbar (35 kPa) and the second type was the alternation between the standard expression setting (again with a maximum under-pressure level of 350 mbar (35 kPa)) and a low energy setting (with a maximum under-pressure level of 150 mbar (15 kPa), when the milk flow is low or non-existent.

The results showed the same average time for the session and the same average collection mass, showing that the high power expression profile is only needed during the times of milk flow, and switching to the low energy mode at other times does not detract from the overall milk expression efficiency.

The milk flow pattern of any individual mother has been shown to be similar, after first start of the milk flow. Therefore, after first determining the milk flow pattern, a program switching between the pump settings can be derived which is optimal for the pattern of that particular user. Thus, instead of continuous adaption of the pump profile, a personalized fixed program may be devised for the mother.

The method above may then become part of a calibration routine. This calibration routine may be applied once only, or periodically. For example, the calibration may be performed when there is mains power, and the fixed program may be used when operating from a battery, to save power.

The method is a non-therapeutic method in that it is only used to enable a mother to express milk for feeding to an infant at a later time.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality.

The mere fact that certain measures are recited in mutually different dependent claims does not indicate that a combination of these measures cannot be used to advantage.

If the term "adapted to" is used in the claims or description, it is noted the term "adapted to" is intended to be equivalent to the term "configured to".

Any reference signs in the claims should not be construed as limiting the scope.

The invention claimed is:

1. A controller for a breast pump device, wherein the controller is for controlling operation of a pressure source of the breast pump device to apply an under-pressure, the controller comprising:

an input for receiving an input signal relating to a milk flow during a breast pumping session using the breast pump device, wherein the input signal indicates at least a characterization of a detected milk flow; and an output for controlling operation of the pressure source in dependence on the input signal, thereby to switch, during the breast pumping, between three modes:

a low energy mode with a first pressure profile of the pressure source;

an expression mode with a second pressure profile of the pressure source; and a stimulation mode with a third, pressure profile of the pressure source wherein the low energy mode has a lower power consumption than the expression mode, wherein the output is for controlling operation of the pressure source to follow a sequence comprising the stimulation mode followed by alternating expression modes and low energy modes.

2. The controller of claim 1, wherein the breast pumping session comprises a continuous sequence of said time periods of the low energy mode and the expression mode after an initial stimulation mode.

3. The controller of claim 2, wherein the low energy mode is the same as the initial stimulation mode.

4. The controller of claim 1, wherein the low energy mode has at least one of a lower maximum under-pressure level, a longer dwell in time, or a longer dwell out time than the expression mode.

5. The controller of claim 1, wherein the expression mode has a maximum under-pressure above 20 kPa and the low energy mode has a maximum under-pressure below 20 kPa.

6. The controller of claim 1, wherein the input signal indicates at least one of: the detection of milk drops; a cumulative milk flow; a milk flow gradient; or a trend in the milk flow gradient.

7. The controller of claim 1, adapted to derive a relationship between the cumulative milk flow and time for a particular user, and to derive a program of operation of the pressure source for the particular user from the relationship.

8. The controller of claim 1, wherein operation of the pressure source is controlled to automatically switch in dependence on the input signal, thereby to automatically switch, during the breast pumping, between three modes.

9. A breast pump device, comprising at least one breast receiving portion configured to receive a breast of a user;

a pressure source coupled to the at least one breast receiving portion and being configured to generate at least an under-pressure;

a sensor for generating said input signal relating to the milk flow during a breast pumping session; and the controller of claim 1.

10. The device of claim 9, wherein the sensor comprises an optical sensor.

11. The device of claim 10, wherein the sensor comprises:

an optical emitter arrangement (Led0-Led2);

an optical detector arrangement (PD0-PD2); and an output for providing a signal indicating the presence milk expressed.

12. The device of claim 9, comprising a battery-operated device.

13. A computer-implemented non-therapeutic method of controlling a breast pump device, the breast pump device comprising at least one breast receiving portion configured to receive a breast of a user and a pressure source coupled to the at least one breast receiving portion and being configured to generate at least an under-pressure, the method comprising:

receiving an input signal relating to a milk flow during a breast pumping session using the breast pump device, wherein the input signal indicates at least a characterization of a detected milk flow; and controlling operation of the pressure source in dependence on the input signal, thereby to switch, during the breast pumping, between:

a low energy mode with a first pressure profile of the pressure source;

an expression mode with a second pressure profile of the pressure source; and a stimulation mode with a third, pressure profile of the pressure source wherein the low energy mode has a lower power consumption than the expression mode, wherein the method comprises controlling operation of the pressure source to follow a sequence comprising the stimulation mode followed by alternating expression modes and low energy modes.

14. The method of claim 13, wherein compared to the expression mode, the low energy mode has at least one of:

a lower electrical power consumption; and at least one of a lower maximum under-pressure level, a longer dwell in time, a longer dwell out time, or a longer rising time.

15. The method of claim 13, wherein the input signal indicates the detection of milk drops or a milk flow level or a milk flow gradient.

16. The method of claim 13, wherein operation of the pressure source is controlled to automatically switch in dependence on the input signal, thereby to automatically switch, during the breast pumping, between three modes.

17. The method of claim 13, wherein the breast pumping session comprises a continuous sequence of said time periods of the low energy mode and the expression mode after an initial stimulation mode.

18. The method of claim 17, wherein the low energy mode is the same as the initial stimulation mode.

19. A computer program comprising computer program code which is adapted to be run on a controller of a breast pump device, the breast pump device comprising:

at least one breast receiving portion configured to receive a breast of a user;

a pressure source coupled to the at least one breast receiving portion and being configured to generate at least an under-pressure; and a sensor for generating an input signal relating to the milk flow during a breast pumping session, wherein the computer program is adapted to implement the method of claim 13.

* * * * *